(12) United States Patent
Vacher et al.

(10) Patent No.: US 8,669,250 B2
(45) Date of Patent: Mar. 11, 2014

(54) DERIVATIVES OF ARYL-{4-HALOGENO-4-[AMINOMETHYL]-PIPERIDIN-1-YL}-METHANONE, THEIR METHOD OF PREPARATION AND THEIR USE AS MEDICINAL PRODUCTS

(75) Inventors: Bernard Vacher, Castres (FR); Francis Colpaert, Puylaurens (FR); Jean-Louis Maurel, Burlats (FR)

(73) Assignee: Pierre Fabre Medicament, Boulogne-Billancourt (FR)

( * ) Notice: Subject to any disclaimer, the term of this patent is extended or adjusted under 35 U.S.C. 154(b) by 174 days.

(21) Appl. No.: 13/376,331

(22) PCT Filed: Jun. 3, 2010

(86) PCT No.: PCT/EP2010/057781
§ 371 (c)(1),
(2), (4) Date: Dec. 5, 2011

(87) PCT Pub. No.: WO2010/139758
PCT Pub. Date: Dec. 9, 2010

(65) Prior Publication Data
US 2012/0115860 A1    May 10, 2012

(30) Foreign Application Priority Data
Jun. 5, 2009 (FR) .................................. 09 53725

(51) Int. Cl.
*C07D 265/36* (2006.01)
*C07D 413/12* (2006.01)
*A61K 31/538* (2006.01)

(52) U.S. Cl.
USPC ........................................ 514/230.5; 544/105

(58) Field of Classification Search
USPC ........................................ 514/230.5; 544/105
See application file for complete search history.

(56) References Cited

U.S. PATENT DOCUMENTS 5,286,735 A    2/1994  Bonnaud et al.
2006/0100244 A1    5/2006  Vacher et al.

FOREIGN PATENT DOCUMENTS

FR    2681325 A1    3/1993
FR    2840900 A1    12/2003

OTHER PUBLICATIONS

Bardin et al., "In the formalin model of tonic nociceptive pain, 8-OH-DPAT produces 5-HT1A receptor-mediated, behaviorally specific analgesia", European Journal of Pharmacology. vol. 421 (2001) pp. 109-114.
Bartsch et al., "Studien zur Chemie der 1,4-Oxazine, 5. Mitt. Zur Chemie 2-substituierter Dihydro-1, 4-benzoxazine", Arch. Pharm., vol. 315, No. 6 (1982) pp. 538-545.
Bourlot et al., "New Substituted 1,4-Benzoxazine Derivatives with Potential Intracellular Calcium Activity", J. Med. Chem., vol. 41 (1998) pp. 3142-3158.
Eliel et al., "Absolute Configuration and Notation", Stereochemistry of Organic Compounds, John Wiley & Sons, Chap. 5 (1994) pp. 104-112.
Glennon, "Serotonin Receptors: Clinical Implications". Neuroscience & Biobehavioral Reviews, vol. 14 (1990) pp. 35-47.
International Search Report mailed in PCT/EP2010/057781 on Aug. 12, 2010.
Koek et al., "5-HT1A receptor activation and antidepressant-like effects: F 13714 has high efficacy and marked antidepressant potential", European Journal of Pharmacology, vol. 420 (2001) pp. 103-112.
Lanfumey et al., "5-HT1 Receptors", Current Drug Targets—CNS & Neurological Disorders, vol. 3 (2004) pp. 1-10.
Millan et al., "Pro- and antinociceptive actions of serotonin (5-HT)1A agonists and antagonists in rodents: relationship to algesiometric paradigm", Behavioural Brain Research, vol. 73 (1996) pp. 69-77.
Piera et al., "Effects of the 5-Hydroxytryptamine1A Receptor Agonists, 8-OH-DPAT, Buspirone and Flesinoxan, upon Brain Damage Induced by Transient Global Cerebral Ischaemia in Gerbils", Arch. Int. Pharmacodyn, vol. 329 (1995) pp. 347-359.
Pollack et al., "Management of Antidepressant-Induced Side Effects: A Practical Guide for the Clinician", J. Clin. Psychiatry, vol. 46, No. 1 (1987) pp. 3-8.
Porsolt et al., "Behavioural Despair in Rats: A New Model Sensitive to Antidepressant Treatments", European Journal of Pharmacology, vol. 47 (1978) pp. 379-391.
Sleight et al., "Identification of 5-hydroxytryptamine1A receptor agents using a composite pharmacopbore analysis and chemical database screening", Nauyn-Shmiedeberg's Arch Pharmacol. vol. 343 (1991) pp. 109-116.
Stahl et al., "Effectiveness of ipsapirone, a 5-HT-1A partial agonist, in major depressive disorder: support for the role of 5-HT-1A receptors in the mechanism of action of serotonergic antidepressants", International Journal of Neuropsychopharmacology, vol. 1 (1998) pp. 11-18.
Zhou et al., "Studies toward the discovery of the next generation of antidepressants. Part 5: 3,4-Dihydro-2H-benzo[1,4]oxazine derivatives with dual 5-HT1A receptor and serotonin transporter affinity", Bicorganic & Medicinal Chemistry Letters, vol. 16 (2006) pp. 1338-1341.

*Primary Examiner* — Kahsay Habte

(74) *Attorney, Agent, or Firm* — Birch, Stewart, Kolasch & Birch, LLP

(57) ABSTRACT

The present invention concerns compounds of general formula (1) (I) wherein R1 is: —a hydrogen atom, or a halogen, —a straight or branched $C_1$-$C_6$ alkyl group or a $C_1$-$C_3$ fluoroalkyl group, —a straight or branched $C_1$-$C_6$ alcoxy group, a carbamyl group, N-substituted or not by one or two, straight or branched $C_1$-$C_3$ alkyl groups, or —a cyano group (CN) R2 is: —a hydrogen atom or a straight or branched $C_1$-$C_6$ alkyl group, $Hal_1$, $Hal_2$ and $Hal_3$ are: —a halogen their addition salts and the hydrates of addition salts with pharmaceutically acceptable mineral acids or organic acids, and their enantiomer forms.

(I)

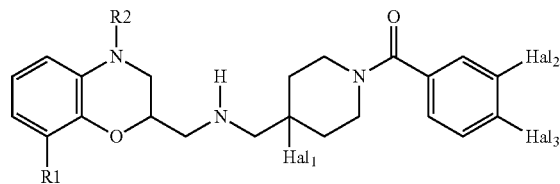

11 Claims, 3 Drawing Sheets

Figure 1:
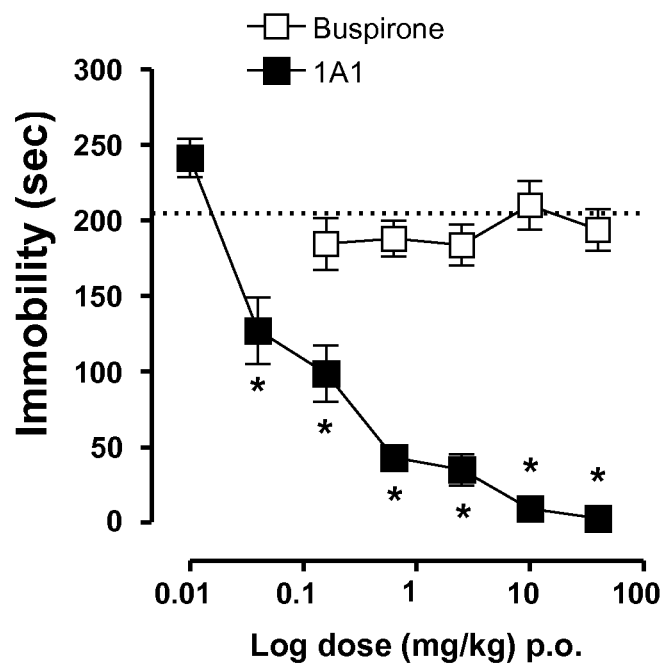

DERIVATIVES OF ARYL-{4-HALOGENO-4-[AMINOMETHYL]-PIPERIDIN-1-YL}-METHANONE, THEIR METHOD OF PREPARATION AND THEIR USE AS MEDICINAL PRODUCTS

The 5-HT$_{1A}$ receptor is structurally, pharmacologically and functionally the serotoninergic receptor that is best characterized. Its involvement in the pathophysiology of numerous disorders and psychiatric illnesses is well known (Curr Drug Targets CNS Neurol Dis. 2004, 3, 1; Neurosci Biobehav Rev. 1990, 14, 35). For example, clinical trials on compounds with agonist activity for serotoninergic receptors of sub-type 5-HT$_{1A}$ have shown that the 5-HT$_{1A}$ agonists are effective in the treatment of anxiety (J. Clin. Psychiatry 1987, 48, 35) and depression (Int. J. Neuropsychopharmacology 1998, 1, 18). In addition, in animals, the 5-HT$_{1A}$ agonists have shown neuroprotective properties (Arch. Int. Pharmacodyn. 1995, 329, 347) and analgesic properties (Behav. Brain Res. 1995, 73, 1/2, 69).

Having regard to the major therapeutic potential of compounds with agonistic activity for the serotoninergic receptors of sub-type 5-HT$_{1A}$, the discovery of novel compounds having said activity is highly desirable.

Although a very high number of compounds have been described as 5-HT1$_A$ agonists, only two are clinically available (i.e. buspirone: Europe and United States and tandospirone: Japan). These two compounds belong to the same chemical family however (i.e., arylpiperazine) and have a relatively similar pharmacological profile: limited affinity for the 5-HT$_{1A}$ receptors and insufficient level of activity in depression and pain models.

It appears that 5-HT$_{1A}$ agonists of different structures have different pharmacological profiles (Eur. J. Pharmacol. 2001, 420, 103-112).

The subject of the present invention is a novel family of compounds derived from aryl-{4-halogeno-4-[aminomethyl]-pipéridin-1-yl}-methanone, which has the following general formula (1):

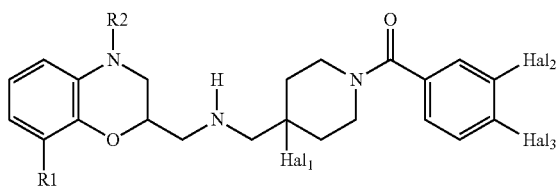

(I)

in which
R1 is:
  a hydrogen atom, or a halogen e.g. a fluorine atom, a chlorine atom, a bromine atom or an iodine atom,
  a straight or branched C$_1$-C$_6$ alkyl group e.g. a straight or branched C$_1$-C$_3$ alkyl group, or a C$_1$-C$_3$ fluoroalkyl group e.g. a fluoromethyl or difluoromethyl or trifluoromethyl group,
  a straight or branched C$_1$-C$_6$ alcoxy group e.g. a straight or branched C$_1$-C$_3$ alcoxy group,
  a carbamyl group, N-substituted or not by one or two, straight or branched C$_1$-C$_3$ alky groups, or
  a cyano group (CN)
R2 is a hydrogen atom or a straight or branched C$_1$-C$_6$ alkyl group e.g. a straight or branched C$_1$-C$_3$ alkyl group,
Hal$_1$, Hal$_2$ and Hal$_3$ are:
  a halogen, for example a fluorine atom, a chlorine atom, a bromine atom or an iodine atom, their addition salts and the hydrates of addition salts with pharmaceutically acceptable mineral acids or organic acids, and their enantiomer forms.

According to the invention, the compounds of general formula (1) are those in which:
Hal$_1$ and Hal$_3$ are:
  a fluorine atom
and Hal$_2$ is:
  a chlorine atom In one particular embodiment of the invention, the formula (1) compounds are those in which:
R1 is:
  a hydrogen atom, or a chlorine atom or a fluorine atom,
  a straight or branched C$_1$-C$_3$ alkyl group, or a fluoromethyl, or difluoromethyl or trifluoromethyl group,
  a straight or branched C$_1$-C$_3$ alcoxy group,
  a carbamyl group (CONH2) N-substituted or not by one or two, straight or branched C$_1$-C$_3$ alkyl groups, or
  a cyano group (CN)
R2 is a hydrogen atom, or a straight or branched C$_1$-C$_3$ alkyl group,
Hal$_1$ and Hal$_3$ are:
  a fluorine atom
and Hal$_e$ is:
  a chlorine atom
their addition salts and the hydrates of addition salts with pharmaceutically acceptable mineral acids or organic acids, and their enantiomer forms.

In another embodiment of the invention, the formula (1) compounds are those in which:
R1 is:
  a hydrogen atom, or a chlorine atom, or a fluorine atom
  a methyl group (CH3)
  a methoxy group (O—CH3)
  a non-substituted carbamyl group (CONH2) or
  a cyano group (CN)
R2 is:
  a hydrogen atom or a methyl group
Hal$_1$ and Hal$_3$ are:
  a fluorine atom
Hal2 is:
  a chlorine atom
their addition salts and the hydrates of addition salts with pharmaceutically acceptable mineral acids or organic acids, and their enantiomer forms.

According to the invention, the compounds of general formula (1) are those in which:
  R1 is chosen from the group consisting of a hydrogen atom, and a carbamyl group N-substituted or not by one or two, straight or branched C$_1$-C$_3$ alkyl groups.

According to the invention, the compounds of general formula (1) are those in which:
  R2 is a hydrogen atom.

According to the invention, the compounds of general formula (1) are those in which:
  R1 and R2 are: a hydrogen atom.

The invention also concerns the mineral or organic salts of the formula (1) compounds and the hydrates of the addition salts, with pharmaceutically acceptable mineral acids or organic acids and their enantiomer forms.

The compounds of the invention contain an asymmetric carbon atom in their structure. On this account they exist in enantiomer form. The invention concerns both each pure enantiomer i.e. associated with less than 5% of the other enantiomer, and the racemic or non-racemic mixtures. However, among the compounds of formula (1), the enantiomer whose carbon atom of the dihydro-benzoxazine methanamine fragment is of absolute configuration (S) is preferred.

The descriptors R and S, used to specify the absolute configuration of the stereogenic carbon atoms contained in the molecules of formula (1), are defined such as defined in the priority rule of Cahn-Ingold-Prelog (E. L. Eliel and S. H. Wilen Stereochemistry of Organic Compounds, John Wiley & Sons, Inc., chap. 5, 104-12, 1994).

By « halogen atom », in the meaning of the present invention, is meant a chlorine atom, a fluorine atom, a bromine atom or an iodine atom.

By « alkyl group », in the meaning of the present invention, is meant a straight or branched, saturated or unsaturated hydrocarbon chain comprising the indicated number of carbons.

By « alcoxy group », in the meaning of the present invention, is meant a straight or branched, saturated or unsaturated hydrocarbon chain bound to an oxygen atom (O-alkyl) and comprising the indicated number of carbons.

By « fluororalkyl group », in the meaning of the present invention, is meant a straight or branched, saturated or unsaturated hydrocarbon chain in which one or more hydrogen atoms have been replaced by a fluorine atom and which comprises the indicated number of carbons.

By « carbamyl group (CONH2) N-substituted or not by one or two, straight or branched $C_1$-$C_2$ alkyl groups », in the meaning of the present invention, is meant the $CONH_2$ group in which the nitrogen atom can be substituted by one or two, straight or branched $C_1$-$C_2$ alkyl groups.

A further subject of the invention concerns pharmaceutical compositions containing, as active ingredient, at least one compound of general formula (1) or one of its pharmaceutically acceptable salts or one of its hydrates of pharmaceutically acceptable salts with pharmaceutically acceptable mineral acids or organic acids, or one of its enantiomers in combination with one or more pharmaceutically acceptable excipients, adjuvants or vehicles. As an example, mention may be made of inclusion complexes in particular those formed by the compounds of the invention and cyclodextrins.

The pharmaceutical compositions of the invention may be compositions which can be administered via oral, nasal, sublingual, rectal or parenteral route. It is generally advantageous to formulate said pharmaceutical compositions in unit dose form. Each dose then contains a predetermined quantity of active ingredient associated with the suitable vehicles, excipients and/or adjuvants, calculated to obtain a given therapeutic effect. As an example of unit dose form which can be administered via oral route, mention may be made of tablets, capsules, granules, powders and oral solutions or suspensions.

The suitable formulations for the chosen form of administration are known and described for example in Remington, The Science and Practice of Pharmacy, 19$^{th}$ Edition, 1995, Mack Publishing Company, and can therefore easily be prepared by persons skilled in the art.

It is known that dosage varies from one person to another, depending on the type and intensity of the disorder, the chosen route of administration, the weight, age and sex of the patient. Therefore, the efficient doses are to be determined in relation to these parameters by specialists in the matter. By way of indication, the efficient doses could range from 0.001 mg/Kg to 100 mg/Kg/day.

The compounds of general formula (1) may exist in several tautomer forms. Said tautomer forms, although not explicitly reported in the present application to simplify formula representation, are nonetheless included in the field of application of the invention.

A further subject of the present invention is a compound of formula (1) or one of its pharmaceutically acceptable salts, or one of its pharmaceutically acceptable salt hydrates with pharmaceutically acceptable mineral acids or organic acids, or one of its enantiomers for its use as medicinal product.

A further subject of the invention is a compound of formula (1) or one of its pharmaceutically acceptable salts or one of its pharmaceutically acceptable salt hydrates with pharmaceutically acceptable mineral acids or organic acids, or one of its enantiomers for its use as medicinal product intended for the treatment of depression.

The subject of the present invention is a formula (1) compound or one of its pharmaceutically acceptable salts or one of its pharmaceutically acceptable salt hydrates with pharmaceutically acceptable mineral acids or organic acids, or one of its enantiomers for its use as medicinal product intended to treat pain.

The subject of the present invention also consists of a formula (1) compound or one of its pharmaceutically acceptable salts or one of its pharmaceutically acceptable salt hydrates with pharmaceutically acceptable mineral acids or organic acids, or one of its enantiomers for its use as medicinal product intended to treat pathological pain and/or physiological pain.

The invention also extends to the synthesis intermediates of formula (2)

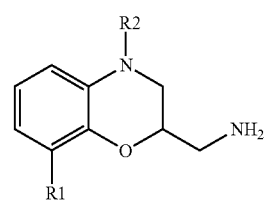

(2)

in which:

R1 is:
 a hydrogen atom,
 a chlorine or fluorine atom, or a straight or branched $C_1$-$C_6$ alkyl group, or a fluoromethyl or difluoromethyl or trifluoromethyl group,
 a straight or branched $C_1$-$C_6$ alcoxy group, or
 a carbamyl group N-substituted or not by one or two, straight or branched $C_1$-$C_3$ alkyl groups, R2 is a hydrogen atom, or a straight or branched $C_1$-$C_6$ alkyl group, used for the preparation of compounds of general formula (1).

The invention extends to the method to prepare compounds of general formula (1):

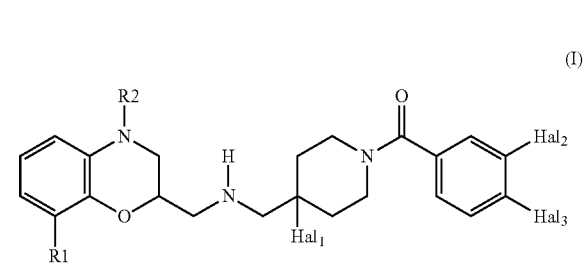

(I)

characterized in that it uses the condensation between an intermediate of type 3,4-dihydro-2H-1,4-benzoxazine-2- methanamine of formula (2) and cyanohydrine of formula (3):

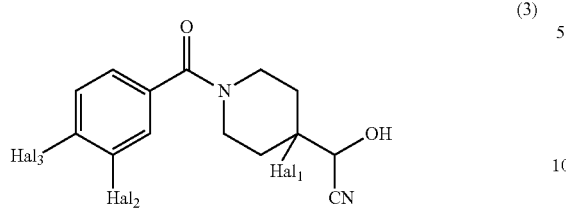

(3)

in the presence of a reducing agent and optionally a base.

The formula (1) compounds were prepared following the reaction sequence indicated in scheme A.

Scheme A

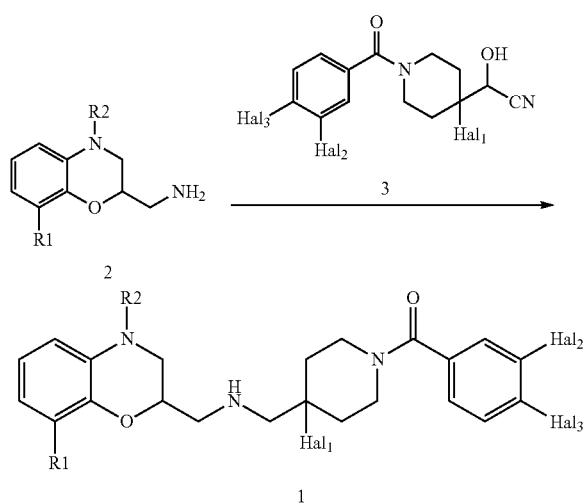

Cyanohydrine (3) is prepared as described in patent WO 02/064585. The fragment 3,4-dihydro-2H-1,4-benzoxazine-2-methanamine of formula (2a) [102908-68-9] is prepared following the method reported in the literature (J. Med. Chem. 1998, 41, 3142). Regarding the novel intermediates of formula (2), these were prepared following the reaction sequence illustrated in scheme B.

Scheme B

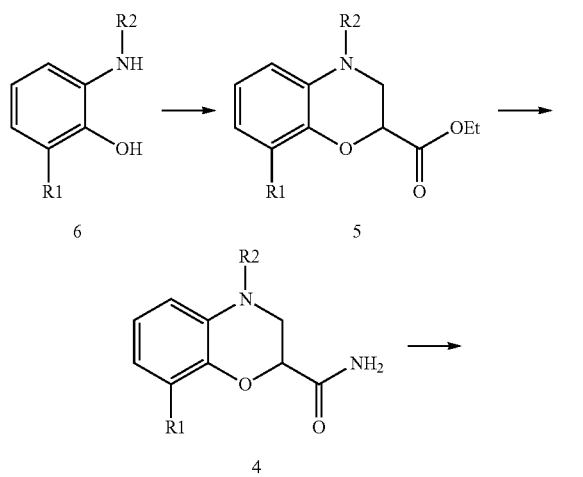

-continued

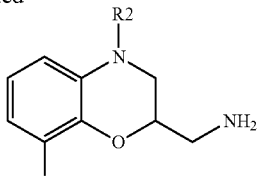

Therefore 2-aminophenol of formula (6) is condensed with ethyl 2,3-dibromo-propionate in a basic medium following the method described in J. Med. Chem. 2003, 16, 1338, to give the ester of formula (5). Compound (5) is then converted to the amide (4) by treatment with ammonia according to a protocol well known to those skilled in the art. The formed amide of formula (4) is then reduced to the expected amine (2) using aluminium lithium hydride in aprotic medium, by analogy with the method described in Archiv der Pharmazie, 1982, 315, 538.

The following examples illustrate the invention but do not in any way limit the invention.

In the examples below:
(i) the progress of the reactions is monitored by thin layer chromatography (TLC) and therefore the reaction times are only given by way of indication.
(ii) different crystalline shapes may give different melting points, the melting points given in the present application are those of products prepared following the described method and are not corrected.
(iii) the structure of the products obtained according to the invention is confirmed by nuclear magnetic resonance (NMR) spectra, centesimal analysis, the purity of the end products is verified by TLC.
(iv) the NMR spectra are recorded in the indicated solvent. Chemical shifts ($\delta$) are expressed in parts per million (ppm) relative to tetramethylsilane. Signal multiplicity is indicated by: s, singlet; d, doublet; t, triplet; q, quadruplet; m, multiplet.
(v) the different unit symbols have their usual meaning: mg (milligram); g (gram); mL (milliliter); cm (centimeter); ° C. (degree Celsius); mmol (millimole); min (minute).
(vi) The abbreviations have the following meaning: MP (melting point); BP (boiling point); Tr (retention time).
(vii) By <<ambient temperature>> is meant a temperature of between 20° C. and 25° C.

Intermediate 1

(+) and (−)-3,4-Dihydro-2H-1,4-benzoxazine-2-methanamine (2a)

The enantiomers of (±)-3,4-dihydro-2H-1,4-Benzoxazine-2-methanamine (8.1 g) are separated by chiral phase chromatography, Chiralpack AD, using as eluting solvent a mixture of hexane-ethanol-diethylamine (90:10:0.05).
(+)-3,4-dihydro-2H-1,4-Benzoxazine-2-methanamine (2a1), 4.0 g; Tr=16.6 min; $[\alpha]_D$=+0.57° (c 0.93, MeOH).
(−)-3,4-dihydro-2H-1,4-Benzoxazine-2-methanamine (2a2), 4.0 g; Tr=21.3 min; $[\alpha]_D$=−0.67° (c.1.34 MeOH).

Intermediate 2

3,4-Dihydro-8-fluoro-2H-1,4-benzoxazine-2-ethyl carboxylate (5b)

A mixture of 2-amino-6-fluorophenol (2 g, 8.3 mmol), of ethyl 2,3-dibromopropionate (1.46 mL, 9.96 mmol) and of K₂CO₃ (3.44 g, 24.9 mmol) in acetone (80 mL) is heated under reflux for 9 h 15 min. The mixture is cooled and filtered. The filtrate is vacuum concentrated, the residue dissolved in iced aqueous NaOH solution (1N, 10 mL) and extracted with ethyl ether. The ethereal phase is washed in water then saline water, dried over MgSO₄ and concentrated under reduced pressure. The residue is purified by filtering though silica gel using dichoromethane as eluting solvent. The title compound is obtained in oil form (1.1 g, 59%).

$^1$H NMR (CDCl₃, 400 MHz) δ 1.26 (t, 3H), 3.61 (m, 2H), 3.87 (s, 1H), 4.26 (q, 2H), 4.88 (t, 1H), 6.37 (d, 1H), 6.53 (t, 1H), 6.67 (t, 1H).

Intermediate 3

3,4-Dihydro-8-fluoro-2H-1,4-benzoxazine-2-carboxamide (4b)

To a solution of 5b (1.1 g, 4.89 mmol) in ethanol (20 mL) an ammonia solution is added (32%, 5 mL). The solution obtained is agitated 14 h at ambient temperature then 10 mL of ammonia are added and the mixture agitated for 48 h. The solution is concentrated under reduced pressure and the residue is dissolved in petroleum ether. The formed precipitate is filtered, washed in petroleum ether and vacuum dried (0.75 g, 78%).

$^1$H NMR (CDCl₃, 400 MHz) δ 1.42 (s, 2H), 3.50 (dd, 1H), 3.73 (dd, 1H), 4.69 (m, 1H), 5.60 (s, 1H), 6.41 (d, 1H), 6.52 (t, 1H), 6.71 (m, 1H).

Intermediate 4

Dihydro-8-fluoro-2H-1,4-benzoxazine-2-methanamine (2b)

To a solution of 4b (0.75 g, 3.83 mmol) in anhydrous THF (20 mL) held at ambient temperature in an inert atmosphere, is added dropwise a solution of LiAlH₄ in THF (13.4 mL, 13.4 mmol). When addition is completed, the mixture is heated to 60° C. for 11 h. The mixture obtained is cooled to 0° C. then an aqueous solution of hydrochloric acid (1N) is added slowly until a pH of 3 is reached. The mixture is concentrated under reduced pressure then the residue is made alkaline through the addition of an aqueous NaOH solution (1N). The mixture is extracted with ethyl acetate, the organic phase is washed with water then with salt water, dried over MgSO₄ and concentrated under reduced pressure. The residue is purified by silica gel chromatography using a dichloromethane-methanol mixture (85:5) as eluting solvent. The title compound is obtained in oil form (1.1 g, 59%).

$^1$H NMR (CDCl₃, 400 MHz) δ 1.42 (s, 2H), 2.98 (m, 2H), 3.26 (dd, 1H), 3.42 (dd, (1H), 3.80 (s, 1H), 4.12 (m, 1H), 6.35, (d, 1H), 6.47 (t, 1H), 6.64 (t, 1H).

Intermediate 5

Dihydro-8-methyl-2H-1,4-benzoxazine-2-carboxamide (4c)

This compound is obtained using the same experimental conditions as those used for the synthesis of intermediate (4b) but replacing 3,4-dihydro-8-fluoro-2H-1,4-benzoxazine-2-ethyl carboxylate (5b) with 3,4-dihydro-8-methyl-2H-1,4-benzoxazine-2-ethyl carboxylate (5c), [220120-58-1]. The title compound of formula (4c) is obtained.

$^1$H NMR (CDCl₃, 400 MHz) δ 1.55 (s, 1H), 2.23 (s, 3H), 3.46 (dd, 1H), 3.67 (dd, 1H), 3.81 (s, 1H), 4.69 (m, 1H), 5.56 (s, 1H), 6.50 (d, 1H), 6.58 (d, 1H), 6.74 (t, 1H).

Intermediate 6

Dihydro-8-methyl-2H-1,4-benzoxazine-2-methanamine (2c)

This compound is obtained using the same experimental conditions as those used for the synthesis of intermediate 2b but by replacing 3,4-dihydro-8-fluoro-2H-1,4-benzoxazine-2-carboxamide (4b) with 3,4-dihydro-8-methyl-2H-1,4-benzoxazine-2-carboxamide (4c). The title compound of formula (2c) is obtained.

$^1$H NMR (CDCl₃, 400 MHz) δ 1.6 (s, 2H), 2.19 (s, 3H), 2.92 (m, 2H), 3.19 (dd, 1H), 3.37 (dd, 1H), 4.11 (m, 1H), 6.17 (d, 1H), 6.54 (d, 1H), 6.67 (t, 1H).

Intermediate 7

Dihydro-8-chloro-2H-1,4-benzoxazine-2-carboxamide (4d)

This compound is obtained using the same experimental conditions as those used for the synthesis of intermediate 4b but replacing 3,4-dihydro-8-fluoro-2H-1,4-benzoxazine-2-ethyl carboxylate (5b) with 3,4-dihydro-8-chloro-2H-1,4-benzoxazine-2-ethyl carboxylate (5d), [73268-47-0]. The title compound of formula (4d) is obtained.

$^1$H NMR (CDCl₃, 400 MHz) δ 3.60 (dd, 1H), 3.85 (dd, 1H), 4.87 (m, 1H), 5.36 (s, 1H), 6.70-6.90 (m, 2H), 6.73 (d, 1H), 7.20 (s, 2H).

Intermediate 8

Dihydro-8-chloro-2H-1,4-benzoxazine-2-methanamine (2d)

This compound is obtained following the same experimental conditions as those used for the synthesis of intermediate 2b but replacing 3,4-dihydro-8-fluoro-2H-1,4-benzoxazine-2-carboxamide (4b) with 3,4-dihydro-8-chloro-2H-1,4-benzoxazine-2-carboxamide (4d). The title compound of formula (2d) is obtained.

$^1$H NMR (CDCl₃, 400 MHz) δ 3.10 (m, 2H), 3.31 (dd, 1H), 3.56 (dd, 1H), 4.16 (m, 1H), 5.11 (s, 2H), 5.28 (s, 1H), 6.70-6.90 (m, 2H), 6.73 (d, 1H).

Intermediate 9

Dihydro-8-methoxy-2H-1,4-benzoxazine-2-methanamine (2e)

This compound is obtained using the same reaction sequence and the same experimental conditions as those used for the synthesis of intermediate 2b but replacing 2-amino-6-fluorophenol with 2-amino-6-methoxyphenol. This gives the title compound of formula (2e).

$^1$H NMR (CDCl₃, 400 MHz) δ 2.98 (m, 2H), 3.23 (dd, 1H), 3.38 (dd, 1H), 3.85 (s, 3H), 4.14 (m, 1H), 4.67 (s, 2H), 6.26 (d, 1H), 6.34 (d, 1H), 6.70 (t, 3H).

Intermediate 10

Dihydro-8-cyano-2H-1,4-benzoxazine-2-methanamine (2f)

This compound is obtained using the same reaction sequence and the same experimental conditions as those used for the synthesis of intermediate 2b but replacing 2-amino-6-fluorophenol with 2-amino-6-cyanophenol. The title compound of formula (2f) is obtained.

$^1$H NMR (CDCl$_3$, 400 MHz) δ 1.48 (s, 2H), 2.99 (m, 2H), 3.28 (dd, 1H), 3.46 (dd, 1H), 4.19 (s, 1H), 4.20 (m, 1H), 6.73-6.80 (m, 2H), 6.90 (d, 1H).

Intermediate 11

Dihydro-4-methyl-2H-1,4-benzoxazine-2-methanamine (2 g)

This compound is obtained following the same experimental conditions as those used for the synthesis of intermediate 2b but replacing 3,4-dihydro-8-fluoro-2H-1,4-benzoxazine-2-carboxamide (4b) with 3,4-dihydro-4-methyl-2H-1,4-benzoxazine-2-carboxamide (4g) [84831-37-8]. The title compound of formula (2g) is obtained.

$^1$H NMR (CDCl$_3$, 400 MHz) δ 2.67-3.16 (m, 3H), 2.85 (s, 3H), 3.38 (d, 1H), 4.3 (s, 1H), 6.55 (t, 1H), 6.63 (d, 1H), 6.70-6.74 (m, 2H), 8.48 (s, 2H).

Intermediate 12

Dihydro-8-carbamoyl-2H-1,4-benzoxazine-2-methanamine (2h)

This compound is obtained following the same experimental conditions as those used for the synthesis of intermediate (2b) but replacing 3,4-dihydro-8-fluoro-2H-1,4-benzoxazine-2-carboxamide (4b) with 3,4-dihydro-4-methyl-2H-1,4-benzoxazine-2-carboxamide (4h). The title compound of formula (2h) is obtained.

$^1$H NMR (DMSO, 400 MHz) δ 1.62 (s, 2H), 2.69-2.83 (m, 2H), 3.07 (dd, 1H), 3.40 (dd, 1H), 4.00 (m, 1H), 6.28 (s, 1H), 6.76-6.84 (m, 3H).

EXAMPLE 1

(−)-(3-Chloro-4-fluoro-phenyl)-{4-fluoro-4-[(3,4-dihydro-2H-1,4-benzoxazine-2-methanamino)-methyl]-pipéridin-1-yl}-methanone (1a1)

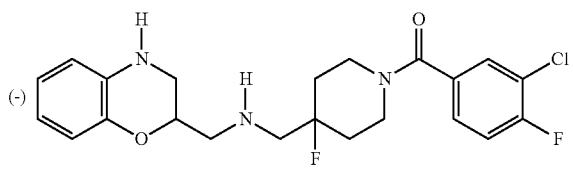 [SMILES: O=C(c1ccc(F)c(Cl)c1)N1CCC(F)(CNCC2CNc3ccccc3O2)CC1]

To a solution of (−)-3,4-dihydro-2H-1,4-benzoxazine-2-methanamine (2a2, 4.1 g, 25 mmol) in methanol (500 mL) are successively added the compound of formula 3 (8.28 g, 26 mmol), iron sulphate (8.3 g, 30 mmol) and sodium cyanoborohydride (2.0 g, 32 mmol). The mixture is heated 6 h at 50° C. then cooled to ambient temperature, filtered and concentrated under reduced pressure. The residue is dissolved in ethyl acetate, washed with water then salt water, dried over MgSO$_4$ and filtered. The solvent is removed by vacuum evaporation and the product is purified by silica chromatography using a dichloromethane-methanol mixture (95:5) as eluting solvent. 1.6 g of the title compound (1a1) is obtained. Salification of this compound with fumaric acid allows the oxalate to be obtained in the form of white crystals (6.0 g).

$C_{22}H_{24}ClF_2N_3O_2$, $C_4H_4O_4$
MP: 185° C.
$[α]_D$=−30.9 (0.4 EtOH).
$^1$H NMR (DMSO d$_6$) δ 1.65-1.93 (m, 4H), 2.76-2.84 (m, 4H), 3.00 (dd, 1H), 3.32 (dd, 1H), 2.74-3.56 (m, 7H), 4.07 (m, 1H), 4.26 (s, 1H), 6.47 (t, 1H), 6.55 (d, 1H), 6.62-6.67 (m, 4H), 7.43-7.51 (m, 2H), 7.66 (d, 1H).
Theoretical % C, 56.58; H, 5.11; N, 7.61.
Actual % C, 56.37; H, 5.16; N, 7.45.

EXAMPLE 2

(+)-(3-Chloro-4-fluoro-phenyl)-{4-fluoro-4-[(3,4-dihydro-2H-1,4-benzoxazine-2-methanamino)-methyl]-piperidin-1-yl}-methanone (1a2)

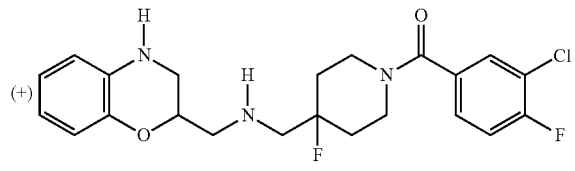 [SMILES: O=C(c1ccc(F)c(Cl)c1)N1CCC(F)(CNCC2CNc3ccccc3O2)CC1]

Using (+)-3,4-dihydro-2H-1,4-benzoxazine-2-methanamine (2a1) instead of (−)-3,4-dihydro-2H-1,4-Benzoxazine-2-methanamine (2a2) the title compound is obtained which is salified with fumaric acid to give the compound of formula (1a2).

$C_{22}H_{24}ClF_2N_3O_2$, $C_4H_4O_4$
MP: 185° C.
$[α]_D$=+37.0 (0.41 MeOH).
$^1$H NMR (DMSO d$_6$) δ 1.65-1.93 (m, 4H), 2.76-2.84 (m, 4H), 3.00 (dd, 1H), 3.32 (dd, 1H), 2.74-3.56 (m, 7H), 4.07 (m, 1H), 4.26 (s, 1H), 6.47 (t, 1H), 6.55 (d, 1H), 6.62-6.67 (m, 4H), 7.43-7.51 (m, 2H), 7.66 (d, 1H).
Theoretical % C, 56.58; H, 5.11; N, 7.61.
Actual % C, 56.78; H, 5.25; N, 7.56.

EXAMPLE 3

(3-Chloro-4-fluoro-phenyl)-{4-fluoro-4-[(3,4-dihydro-2H-1,4-benzoxazine-2-methanamino)-methyl]-piperidin-1-yl}-methanone (1a3)

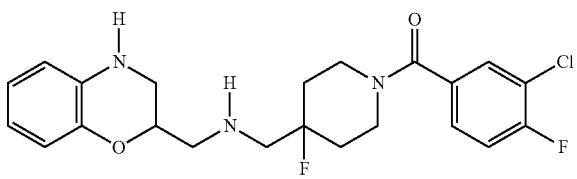

Using 3,4-dihydro-2H-1,4-benzoxazine-2-methanamine, commercially available, instead of (−)-3,4-dihydro-2H-1,4-Benzoxazine-2-methanamine (2a2), the title compound is obtained which is salified with hydrochloric acid to give the compound of formula (1a3).

$C_{22}H_{24}ClF_2N_3O_2$, $H_2Cl_2$
MP: 175° C.
$^1$H NMR (DMSO d$_6$) δ 1.68-2.14 (m, 4H), 3.12-3.21 (m, 4H), 3.37-3.50 (3, 7H), 4.32 (s, 1H), 4.58 (m, 1H), 6.59 (t, 1H), 6.71 (d, 1H), 6.74-6.77 (m, 2H), 7.44-7.55 (m, 2H), 7.70 (dd, 1H), 9.48 (s, 2H).

Theoretical % C, 51.93; H, 5.15; N, 8.26.
Actual % C, 5.81; H, 5.30; N, 8.22.

EXAMPLE 4

(3-Chloro-4-fluoro-phenyl)-{4-fluoro-4-[(3,4-dihydro-2H-8-fluoro-1,4-benzoxazine-2-methanamino)-methyl]-piperidin-1-yl}-methanone (1b)

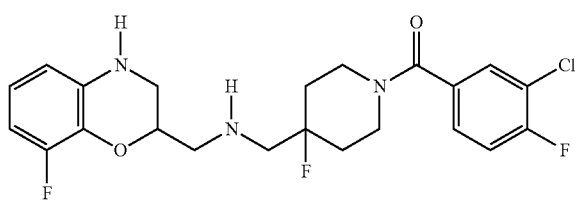 [SMILES: O=C(c1ccc(F)c(Cl)c1)N1CCC(F)(CNCC2CNc3cccc(F)c3O2)CC1]

The same operating mode is used as for the preparation of (−)-(3-chloro-4-fluoro-phenyl)-{4-fluoro-4-[(3,4-dihydro-2H-1,4-benzoxazine-2-methanamino)-methyl]-piperidin-1-yl}-methanone (1a1) but by replacing (−)-3,4-dihydro-2H-1,4-benzoxazine-2-methanamine (2a2) with (±)-dihydro-8-fluoro-2H-1,4-benzoxazine-2-methanamine (2b). The compound obtained is then salified to fumarate form.

$C_{22}H_{23}ClF_3N_3O_2$, $C_4H_4O_4$
MP: 100° C.
$^1$H NMR (DMSO $d_6$) δ 1.61-2.00 (m, 4H), 2.76-2.84 (m, 4H), 3.03-3.45 (m, 9H), 4.06 (m, 1H), 4.23 (s, 1H), 5.96 (s, 1H), 6.34-6.38 (m, 2H), 6.59-6.63 (m, 2H), 7.43-7.49 (m, 2H), 7.67 (d, 1H).
Theoretical % C, 54.79; H, 4.77; N, 7.37.
Actual % C, 54.57; H, 4.88; N, 7.13.

EXAMPLE 5

(3-Chloro-4-fluoro-phenyl)-{4-fluoro-4-[(3,4-dihydro-2H-8-methyl-1,4-benzoxazine-2-methanamino)-methyl]-piperidin-1-yl}-methanone (1c)

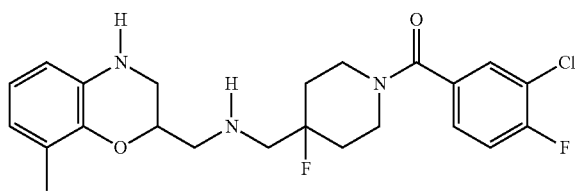 [SMILES: Cc1cccc2c1OC(CNCC1(F)CCN(C(=O)c3ccc(F)c(Cl)c3)CC1)CN2]

The same operating mode is followed as for the preparation of (−)-(3-chloro-4-fluoro-phenyl)-{4-fluoro-4-[(3,4-dihydro-2H-1,4-benzoxazine-2-methanamino)-methyl]-piperidin-1-yl}-methanone (1a1) but by replacing (−)-3,4-dihydro-2H-1,4-benzoxazine-2-methanamine (2a2) with dihydro-8-methyl-2H-1,4-benzoxazine-2-methanamine (2c). The compound obtained is then salified to dihydrochloride form.

$C_{23}H_{26}ClF_2N_3O_2$, $H_2Cl_2$
MP: 180° C.
$^1$H NMR (DMSO $d_6$) δ 1.85-2.08 (m, 4H), 2.13 (s, 3H), 3.09-3.46 (m, 10H), 4.31 (s, 1H), 4.59 (m, 1H), 6.50-6.55 (m, 2H), 6.63-6.67 (m, 1H), 7.45-7.54 (m, 2H), 7.69 (d, 1H), 9.52 (s, 2H).
Theoretical % C, 52.84; H, 5.40; N, 8.04.
Actual % C, 53.55; H, 5.67; N, 7.65.

EXAMPLE 6

(3-Chloro-4-fluoro-phenyl)-{4-fluoro-4-[(3,4-dihydro-2H-8-chloro-1,4-benzoxazine-2-methanamino)-methyl]-piperidin-1-yl}-methanone (1d)

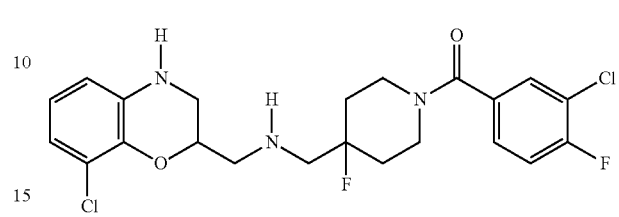

The same operating mode is used as for the preparation of (−)-(3-chloro-4-fluoro-phenyl)-{4-fluoro-4-[(3,4-dihydro-2H-1,4-benzoxazine-2-methanamino)-methyl]-piperidin-1-yl}-methanone (1a1) but by replacing (−)-3,4-dihydro-2H-1,4-benzoxazine-2-methanamine (2a2) with dihydro-8-chloro-2H-1,4-benzoxazine-2-methanamine (2d). The compound obtained is then salified to dihydrochloride form.

$C_{22}H_{23}Cl_2F_2N_3O_2$, $H_2Cl_2$
MP: 136° C.
$^1$H NMR (DMSO $d_6$) δ 1.82-1.94 (m, 4H), 3.11-3.75 (m, 10H), 4.06 (m, 1H), 4.35 (s, 1H), 4.64 (m, 1H), 6.57-6.64 (m, 2H), 6.73 (m, 1H), 7.45-7.68 (m, 2H), 7.68 (d, 1H), 9.59 (d, 2H).
Theoretical % C, 48.63; H, 4.64; N, 7.73.
Actual % C, 48.57; H, 4.54; N, 7.42.

EXAMPLE 7

(3-Chloro-4-fluoro-phenyl)-{4-fluoro-4-[(3,4-dihydro-2H-8-methoxy-1,4-benzoxazine-2-methanamino)-methyl]-piperidin-1-yl}-methanone (1e)

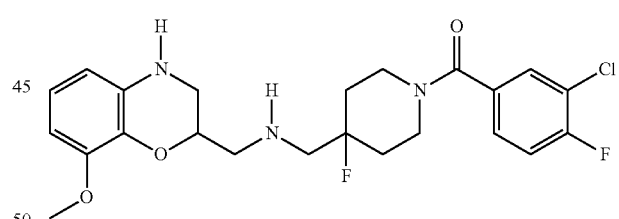

The same operating mode is followed as for the preparation of (−)-(3-chloro-4-fluoro-phenyl)-{4-fluoro-4-[(3,4-dihydro-2H-1,4-benzoxazine-2-methanamino)-methyl]-piperidin-1-yl}-methanone (1a1) but by replacing (−)-3,4-dihydro-2H-1,4-benzoxazine-2-methanamine (2a2) with dihydro-8-methoxy-2H-1,4-benzoxazine-2-methanamine (2e). The compound obtained is the salified to dihydrochloride form.

$C_{23}H_{26}ClF_2N_3O_3$, $H_2Cl_2$
MP: 187° C.
$^1$H NMR (DMSO $d_6$) δ 1.75-2.10 (m, 4H), 3.09-3.70 (m, 10H), 3.71 (s, 3H), 4.27 (s, 1H), 4.59 (m, 1H), 6.31-6.36 (m, 2H), 6.68 (t, 1H), 7.46-7.53 (m, 2H), 7.69 (d, 1H), 9.86 (s, 2H).
Theoretical % C, 51.26; H, 5.24; N, 7.79.
Actual % C, 51.15; H, 5.37; N, 7.53.

EXAMPLE 8

(3-Chloro-4-fluoro-phenyl)-{4-fluoro-4-[(3,4-dihydro-2H-8-cyano-1,4-benzoxazine-2-methanamino)-methyl]-piperidin-1-yl}-methanone (1f)

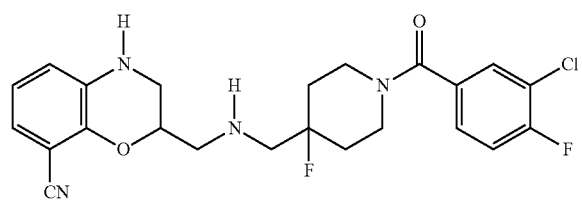 [SMILES: N#Cc1cccc2c1OC(CNCC1(F)CCN(C(=O)c3ccc(F)c(Cl)c3)CC1)CN2]

The same operating mode is followed as for the preparation of (−)-(3-chloro-4-fluoro-phenyl)-{4-fluoro-4-[(3,4-dihydro-2H-1,4-benzoxazine-2-methanamino)-methyl]-piperidin-1-yl}-methanone (1a1) but by replacing (−)-3,4-dihydro-2H-1,4-benzoxazine-2-methanamine (2a2) with dihydro-8-cyano-2H-1,4-benzoxazine-2-methanamine (2f). The compound obtained is then salified to dihydrochloride form.

$C_{23}H_{23}ClF_2N_4O_2, H_2Cl_2$ 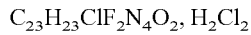

MP: 149° C.

$^1$H NMR (DMSO $d_6$) δ 1.72-2.13 (m, 4H), 3.14-3.63 (m, 10H), 4.26 (s, 1H), 4.72 (m, 1H), 6.87-6.94 (m, 3H), 7.45-7.64 (m, 2H), 7.67 (d, 1H), 9.60 (s, 2H).

Theoretical % C, 51.75; H, 4.72; N, 10.50.

Actual % C, 51.36; H, 4.71; N, 10.28.

EXAMPLE 9

(3-Chloro-4-fluoro-phenyl)-{4-fluoro-4-[(3,4-dihydro-2H-4-methyl-1,4-benzoxazine-2-methanamino)-methyl]-piperidin-1-yl}-methanone (1g)

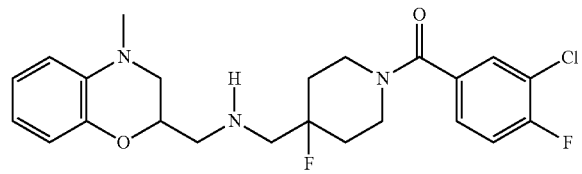 [SMILES: CN1CC(CNCC2(F)CCN(C(=O)c3ccc(F)c(Cl)c3)CC2)Oc2ccccc21]

The same operating mode is followed as for the preparation of (−)-(3-chloro-4-fluoro-phenyl)-{4-fluoro-4-[(3,4-dihydro-2H-1,4-benzoxazine-2-methanamino)-methyl]-piperidin-1-yl}-methanone (1a1) but by replacing (−)-3,4-dihydro-2H-1,4-benzoxazine-2-methanamine (2a2) with dihydro-4-methyl-2H-1,4-benzoxazine-2-methanamine (2g). The compound obtained is then salified to fumarate form.

$C_{23}H_{26}ClF_2N_3O_2, C_4H_4O_4$ 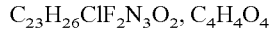

MP: 125° C.

$^1$H NMR (DMSO $d_6$) δ 1.60-2.08 (m, 4H), 2.81 (s, 3H), 2.76-3.51 (m, 10H), 4.22 (m, 2H), 6.56-6.76 (m, 4H), 7.46-7.65 (m, 2H), 7.67 (d, 1H).

Theoretical % C, 48.80; H, 5.34; N, 7.42.

Actual % C, 48.72; H, 5.42; N, 7.33.

EXAMPLE 10

(3-Chloro-4-fluoro-phenyl)-{4-fluoro-4-[(3,4-dihydro-2H-8-carbamoyl-1,4-benzoxazine-2-methanamino)-methyl]-piperidin-1-yl}-methanone (1h)

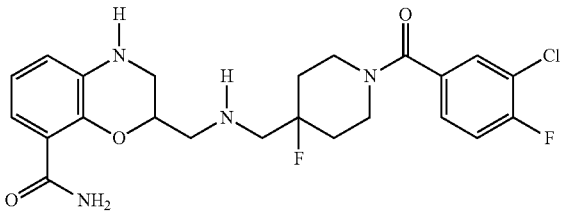 [SMILES: NC(=O)c1cccc2c1OC(CNCC1(F)CCN(C(=O)c3ccc(F)c(Cl)c3)CC1)CN2]

The same operating mode is followed as for the preparation of (−)-(3-chloro-4-fluoro-phenyl)-{4-fluoro-4-[(3,4-dihydro-2H-1,4-benzoxazine-2-methanamino)-methyl]-piperidin-1-yl}-methanone (1a1) but by replacing (−)-3,4-dihydro-2H-1,4-benzoxazine-2-methanamine (2a2) with dihydro-8-carbamoyl-2H-1,4-benzoxazine-2-methanamine (2h). The compound obtained is then salified to dihydrochloride form.

$C_{23}H_{25}ClF_2N_4O_3, H_2Cl_2$ 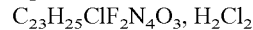

MP: 170° C.

$^1$H NMR (DMSO $d_6$) δ 1.80-2.12 (m, 4H), 3.12-3.73 (m, 10H), 4.45 (s, 1H), 4.64 (m, 1H), 6.87-6.93 (m, 3H), 7.45-7.66 (m, 2H), 7.68 (d, 1H), 9.40 (d, 2H).

Theoretical % C, 50.06; H, 4.93; N, 10.15.

Actual % C, 4973; H, 4.68; N, 10.00.

Pharmacological Study on the Products of the Invention

The compounds of this invention were compared with buspirone (4-butyl-4-methyl-1-[4-(4-pydi urid-2-yl-piperazin-1-yl)-butyl]-piperidine-2.6-dione) which is an agonist of 5-HT$_{1A}$ receptors used clinically. The affinity of the compounds of the invention for the rat 5-HT$_{1A}$ receptor was measured conventionally from competitive experiments with a radiolabelled 5-HT$_{1A}$ agonist. The antidepressant activity of the compounds of the invention and of buspirone was assessed after oral administration in rats with the forced swimming test (Eur. J. Pharmacol. 1978, 47, 379). This test is widely used since it is predictive of antidepressant action in man. Analgesic activity was determined after intra-peritoneal administration to rats, both with a physiological pain model and a pathological pain model. By physiological pain, the inventors designate pain whose origin is a lesion and/or organic ill-function such as pain caused by excessive nociceptive stimuli. On the contrary, by pathological pain the inventors designate pain which has no apparent pathological cause and therefore does not play a physiological role (e.g. alarm signal); this latter category includes some pain of neuropathic origin for example.

The physiological pain model chosen by the inventors to determine the analgesic activity of the compounds of the invention uses excess nociceptive stimuli (injection of formol) to cause a painful sensation in animal (Eur. J. Pharmacol. 2001, 421, 109). For the so-called pathological pain model in animal, the inventors chose to use pain induced by the injection of a cytotoxic agent such as oxaliplatine (Eur. J. Cancer 2007, 2658).

1—Measurement of the Affinity of the Compounds of the Invention for the 5-HT$_{1A}$ Receptors Protocol The in vitro affinity of the compounds of the invention for the 5-HT$_{1A}$ receptors was determined by measuring the shift of ($^3$H)8-OH-DPAT (agonist of $5HT_{1A}$ receptors labelled with tritium, TRK 850; 160-240 Ci/mmole).

The study on binding with the $5-HT_{1A}$ receptor was conducted as described in Naunyn-Schmiedeberg's Arch. Pharmaco. 1991, 343, 106. For these experiments, rat cerebral cortices were used. After unfreezing the brain in Tris-HCl buffer 50 mmol, pH=7.40 at 25° C., the cerebral cortex is sampled and homogenized in 20 volumes of buffer held at 4° C. The homogenate is centrifuged at 39000 g for 10 min, the centrifuge residue is suspended in the same volume of buffer and again centrifuged. After further suspension under the same conditions, the homogenate is incubated for 10 min at 37° C. then again centrifuged. The final residue is suspended in cold reaction buffer Tris-HCl 50 mmol, pH=7.40 at 25° C. containing 10 mmol of pargyline, 4 mmol of $CaCl_2$ and 0.10% ascorbic acid. The final concentration of the tissue in the incubation medium is 10 mg/tube.

The reaction tubes contain 0.10 mL of ($^3$H)8-OH-DPAT (final 0.20 mmol), 0.10 mL of product to be tested 6-7 concentrations and 0.80 mL of tissue. Non-specific binding is defined using 10 mmol of 5-HT. The reaction tubes are incubated at 23° C. for 30 min then their content is rapidly vacuum filtered through Whatman GF/B filters, the tubes are rinsed with 2×5 mL of Tris-HCl buffer 50 mmol, pH=7.4 at 25° C. Radioactivity is collected on the filter and analyzed by liquid scintillation by adding 4 mL of scintillating liquid (Emulsifier Safe, Packard). All experiments were performed in triplicate.

The inhibition constants (Ki) of the products of the invention are estimated from shift experiments using the non-linear regression programme RADLIG version 4 by EBDA (Equilibrium Binding Data Analysis Biosoft, Cambridge, UK, Mc Pherson, 1985). The dissociation constant of the radioactive ligand used for calculations is 0.31 mmol for ($^3$H)8-OH-DPAT. The values of pKi (−log Ki) are given in the form mean±SEM of at least 3 experiments.

2—Forced Swimming Test: Antidepressant Activity of the Compounds of the Invention Protocol The rats (Male Sprague Dawley rats (ICO: OFA SD [IOPS], Iffa Credo, France), are placed in a cylinder (45 cm high and 20 cm in diameter) filled with water at 25° C.±0.5 up to a height of 17 cm. This depth allows rats to swim or float without their tail touching the bottom of the cylinder.

24 h before the test day, the rats are placed in the cylinder for 15 min, a lapse of time after which they no longer attempt to escape and remain immobile. On the test day the animals are replaced in the cylinder and the duration of animal immobility is measured by direct observation followed by verification of an audiovisual recording for 5 min. The products of the invention are administered by oral route 60 min before the test. A rat is considered to be immobile if it allows itself to float and only makes small movements to remain on the surface. Two rats are observed at the same time.

3—Formol Test: Analgesic Activity Against So-Called Physiological Pain

Protocol

The rats (Male Sprague Dawley rats (ICO: OFA SD [IOPS], Iffa Credo, France) are placed in plexiglass observation boxes above an angled mirror so as to facilitate observation of the hind paws. After thirty minutes of habituation, the animals are given an injection of formol diluted to 2.5% on the plantar surface of the right hind paw. The injection of formol produces behavioural responses which occur in two phases:

an acute phase, from 0 to 5 min after injection of the formol, corresponding to stimulation of receptors specialized in the transmission of pain messages to the spinal cord.

a late phase which occurs 20 to 30 min after the injection. This phase corresponds to stimulation of receptors by inflammatory mediators and/or to hyper-excitability of the dorsal horn induced during the first phase. This late phase therefore involves central sensitization.

For the study of the compounds of the invention we selected two expressions of painful behaviour and chose two periods of observation which correspond to the two pain phases (i.e. 0-5 min and 22.5-27.5 min). During these two 5-min periods the animals are observed every 30 seconds and are given scores for the following behaviours: paw licking or not of the injected paw, and lifting or non-lifting of the injected paw. Ten observations give a maximum score of 10 for each parameter for each of the 2 phases. The products of the invention are administered via intraperitoneal route 15 min before the injection of formol.

4—Oxaliplatine Test: Analgesic Activity Against So-Called Pathological Pain

Protocol

The rats (Male Sprague Dawley rats (ICO: OFA SD [IOPS], Iffa Credo, France) are tested a first time on the Friday to determine their mechanical sensitivity threshold (von Frey test). They are then given an intra-peritoneal injection (i.p.) of oxaliplatine (anticancer treatment causing neuropathic pain in patients) at a dose of 8 mg/kg. This dose in rat induces neuropathy which translates as mechanical hypersensitivity (allodynia) which develops 3 days after the injection with a peak on day five. For the study of the compounds of the invention, the animals are re-tested on day five, 15 min after administration of the compound via intra-peritoneal route.

Statistical Analyses of Results

Quantification of the effect of the compounds of the invention on the forced swimming tests and on the formol test is conducted by one-factor variance analysis between groups (ANOVA analysis) followed by a multiple comparison test (Dunnett's test) versus control animals. The $ED_{50}$ value is calculated using Litchfield and Wilcoxon analysis from the percentage of responding animals.

FIGURES

FIG. 1 gives the results obtained during the forced swimming test after oral administration (p.o.) of the compound of formula (1a1) or of buspirone, namely the observed time of animal immobility (in seconds) compared with the logarithm of the dose of the administered compound (in mg/kg).

Figure 2:
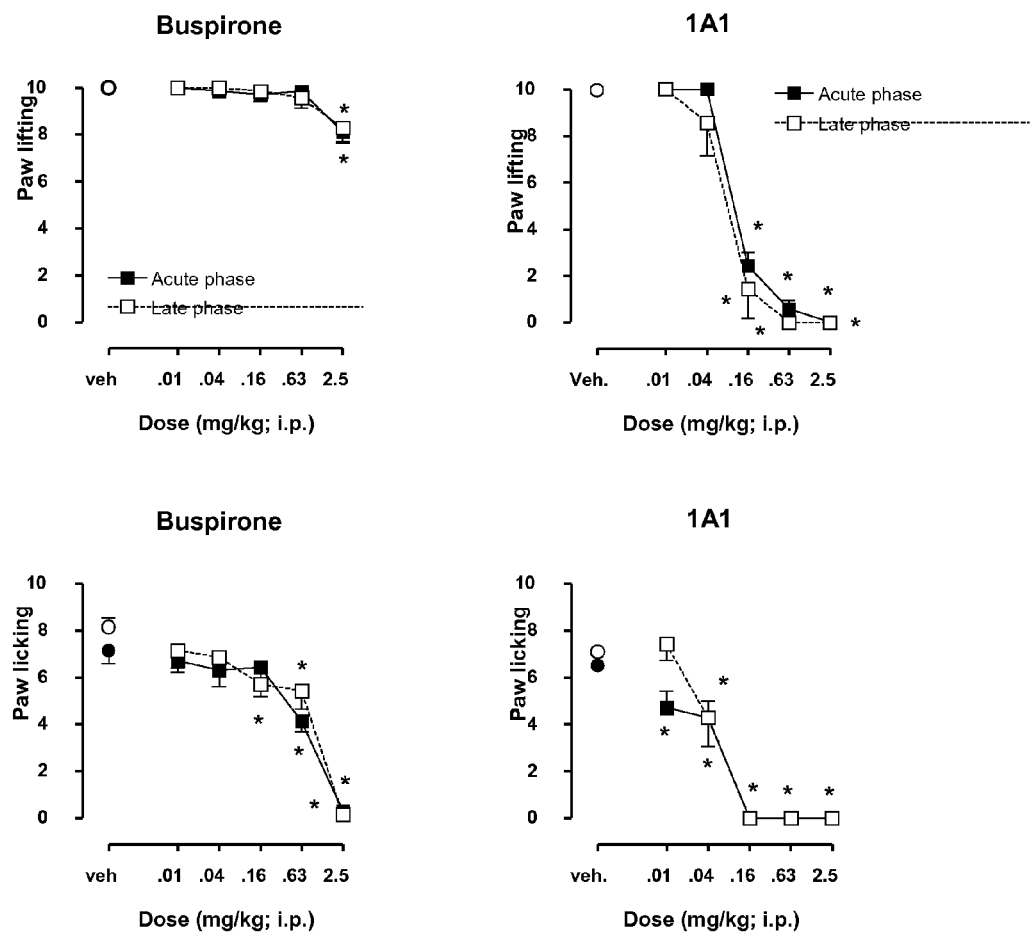

FIG. 2 gives the observed results (either for paw lifting or paw licking) for the formol test after intra-peritoneal administration (i.p.) of the compound of formula (1a1) or of buspirone. For this test, the animals are observed every 30 seconds during two periods of 5 min. The following behaviours are noted: paw licking or not of the injected paw, and paw lifting or not of the injected paw. Ten observations give a maximum score of 10 for each parameter for each of the 2 phases, measuring either paw lifting or paw licking. This test was also performed by comparison with administration of the vehicle (veh) alone.

Figure 3:
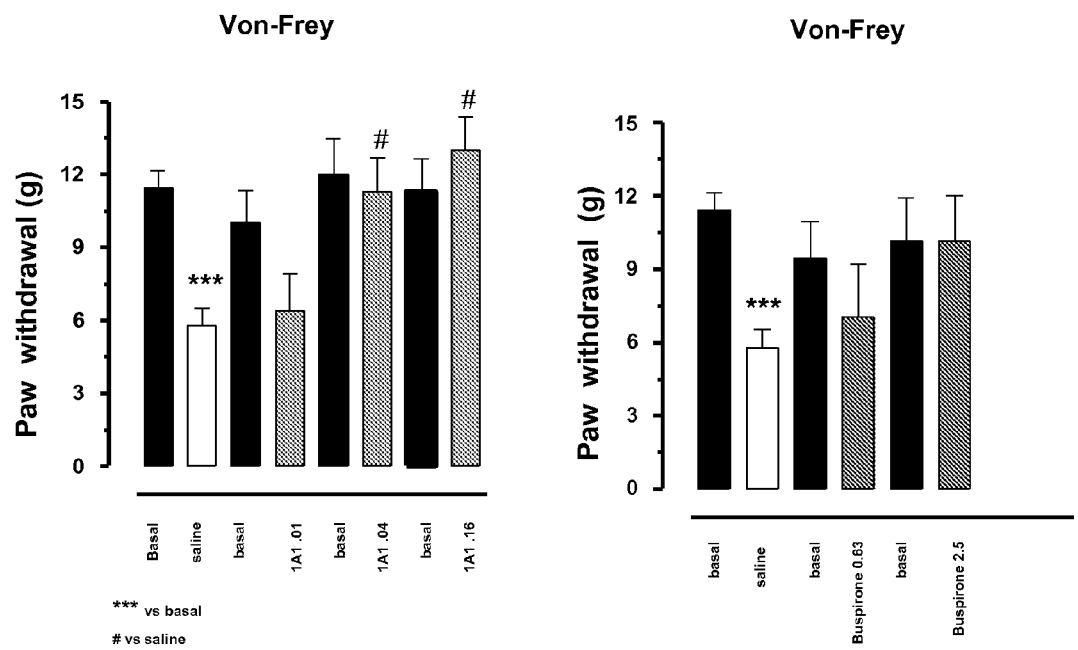

FIG. 3 shows the results obtained with the von Frey test with oxaliplatine. For each experiment, pressure is exerted on the paw of the animals, either non-treated with oxaliplatine (basal), or treated with oxaliplatine and after intra-peritoneal administration of a saline solution or of compound (1a1) (at a dose of 0.01, 0.04 or 0.16 mg/kg) or of buspirone (at a dose of 0.63 or 2.5 mg/kg). The pressure force is then measured (in g) at which withdrawal of the paw of the animals is observed.

RESULTS

1) Measurement of the Affinity of the Compounds of the Invention for the 5-HT$_{1A}$ Receptors.

Table 1, as an example, gives the pKi values for some derivatives of the invention compared with buspirone chosen as reference product.

TABLE 1

| Compound | 5-HT$_{1A}$ affinity (pKi) |
|---|---|
| 1a1 | 8.99 |
| 1b | 9.20 |
| 1c | 8.91 |
| 1d | 8.64 |
| 1e | 8.82 |
| 1f | 9.19 |
| 1g | 9.10 |
| 1h | 9.13 |
| buspirone | 7.65 |

The test results show that the compounds of formula (1) have strong affinity for the serotoninergic receptors of sub-type 5-HT$_{1A}$. The 5-HT$_{1A}$ affinity of the compounds of the invention is additionally much higher than that of buspirone.

2) Forced Swimming Test: Antidepressant Activity of the Compounds of the Invention.

The forced swimming test (FIG. 1), after oral administration in the rat, shows that the compound of formula (1a1), representing the series, exerts central action. For example, the formula (1a1) compound is capable of reducing the animal's immobility time in dose-dependent fashion [F(7.50)=43.67; P<0.001]. This compound is both very powerful (ED$_{50}$=0.08 mg/Kg) and highly efficient since none of the animals remains immobile on and after the dose of 10 mg/Kg. By comparison buspirone, even at a dose of 40 mg/Kg, has no effect on animal immobility [F(5.61)=0.51 P>0.05]. To conclude, compound (1a1), and the compounds belonging to this chemical series in general, exhibit fully remarkable antidepressant properties after administration via oral route.

3) Formol Test: Analgesic Activity Against So-Called Physiological Pain.

The formol test (FIG. 2), using administration via intra-peritoneal route, shows that the formula (1a1) compound, representing this chemical series, exerts remarkable analgesic activity against pain of physiological origin. The formula (1a1) compound shows dose-dependent inhibition of the 2 measured parameters (paw lifting and paw licking) for each of the 2 phases: [F(5.36)=323.80; P<0.001], [F(5.36)=41.13; P<0.001], [F(5.36)=50.19; P<0.001] and [F(5.36)=39.67; P<0.001], respectively.

The efficiency of the formula (1a1) compound and of the compounds of the invention in general, is clearly apparent with regard to the paw lifting parameter. Compound (1a1) not only proves to be very powerful (ED$_{50}$=0.05 mg/Kg) for inhibition of this parameter, but it is also very efficient insofar as it prevents paw lifting in all the rats injected with formol on and after a dose of 0.63 mg/Kg. Full analgesia is obtained irrespective of the pain phase under consideration (acute or late) and is also expressed for the paw licking parameter. By comparison, buspirone only affects the paw lifting parameter during the acute phase and late phase on and after a dose of 2.5 mg/kg ([F(3.24)=8.20; P<0.001] and [F(3.24)=4.57; P=0.01]). Buspirone inhibits paw licking on and after a dose of 0.63 mg/kgfor the acute phase and 2.5 mg/kg for the late phase ([F(3.24)=47.04; P<0.001] and [F(3.24)=40.50; P<0.001]). To conclude, compound (1a1), and the compounds belonging to this chemical series in general, exhibit analgesic properties against physiological pain that are fully remarkable after intra-peritoneal administration.

4-) Oxaliplatine Test: Analgesic Activity Against So-Called Pathological Pain.

The test for oxaliplatine-induced pain (FIG. 3), via intraperitoneal administration, shows that the formula (1a1) compound, representative of this chemical series, exerts powerful analgesic activity against so-called pathological pain. For example the formula (1a1) compound shows dose-dependent inhibition of allodynia developed by animals treated with oxaliplatine. Full analgesia is obtained on and after a dose of 0.04 mg/kg of compound 1a1. By comparison, buspirone does not produce any significant analgesia even at a dose of 2.5 mg/kg.

To summarize, compound (1a1), and the compounds belonging to this chemical series in general, display analgesic properties against pathological pain that are fully remarkable after administration via i.p. route.

It arises from these tests that the compounds of the invention exhibit:
- affinity for the serotoninergic receptors of sub-type 5-HT$_{1A}$ that is greater than that of buspirone,
- antidepressant activity that is greater than that of buspirone,
- broad analgesic activity since it addresses pain of both physiological and pathological origin. This analgesic activity proves to be greater than that of buspirone, a 5-HT$_{1A}$ agonist given human clinical use.

In this respect, the compounds of the invention are therefore potentially useful for the treatment of pathologies involving serotoninergic ill-functioning, in particular for the treatment of depression and pain for which therapeutic needs are considerable.

The administration of the compounds of the invention can use oral, nasal, sublingual, rectal or parenteral routes. As a non-limiting example of formulations, one preparation of the compounds of the invention is given below. The ingredients and other therapeutically acceptable ingredients can be added in other proportions without modifying the scope of the invention. The terms <<active ingredient>> used in the examples of formulation given below refer to a compound of formula (1) or an addition salt or optionally to a hydrate of an addition salt of the formula (1) compound with a pharmaceutically acceptable mineral acid or organic acid or one of the enantiomers of the formula (1) compound.

Example of Pharmaceutical Composition:

Formula to prepare 1000 tablets each containing 10 mg of active ingredient:

| | |
|---|---|
| Active ingredient | 10 g |
| Lactose | 100 g |
| Wheat starch | 10 g |
| Magnesium stearate | 3 g |
| Talc | 3 g |

The invention claimed is:

1. Compounds of formula (1)

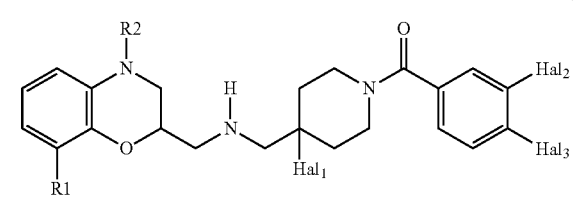

wherein
R1 is:
  a hydrogen atom or a halogen, a straight or branched $C_1$-$C_6$ alkyl group or a $C_1$-$C_3$ fluoroalkyl group, a straight or branched $C_1$-$C_6$ alcoxy group, a carbamyl group, N-substituted or not by one or two, straight or branched $C_1$-$C_3$ alkyl groups, or a cyano group (CN)

R2 is a hydrogen atom or a straight or branched $C_1$-$C_6$ alkyl group, $Hal_1$, $Hal_2$ and $Hal_3$ are:

a halogen their addition salts and the hydrates of addition salts with pharmaceutically acceptable mineral acids or organic acids, and their enantiomer forms.

2. Compound according to claim 1, characterized in that $Hal_1$ and $Hal_3$ are a fluorine atom and $Hal_2$ is a chlorine atom.

3. Compound according to claim 1, characterized in that R1 is chosen from the group consisting of: a hydrogen atom and a carbamyl group N-substituted or not by one or two, straight or branched $C_1$-$C_3$ alkyl groups.

4. Compound according to claim 1, characterized in that R2 is a hydrogen atom.

5. Compound according to claim 1, characterized in that R1 and R2 are a hydrogen atom.

6. Compound according to claim 1, characterized in that it is chosen from the group consisting of:
- (−)-(3-Chloro-4-fluoro-phenyl)-{4-fluoro-4-[(3,4-dihydro-2H-1,4-benzoxazine-2-methanamino)-methyl]-piperidin-1-yl}-methanone,
- (+)-(3-Chloro-4-fluoro-phenyl)-{4-fluoro-4-[(3,4-dihydro-2H-1,4-benzoxazine-2-methanamino)-methyl]-piperidin-1-yl}-methanone,
- (3-Chloro-4-fluoro-phenyl)-{4-fluoro-4-[(3,4-dihydro-2H-1,4-benzoxazine-2-methanamino)-methyl]-piperidin-1-yl}methanone,
- (3-Chloro-4-fluoro-phenyl)-{4-fluoro-4-[(3,4-dihydro-2H-8-fluoro-1,4-benzoxazine-2-methanamino)-methyl]-piperidin-1-yl}-methanone,
- (3-Chloro-4-fluoro-phenyl)-{4-fluoro-4-[(3,4-dihydro-2H-8-methyl-1,4-benzoxazine-2-methanamino)-methyl]-piperidin-1-yl}-methanone,
- (3-Chloro-4-fluoro-phenyl)-{4-fluoro-4-[(3,4-dihydro-2H-8-chloro-1,4-benzoxazine-2-methanamino)-methyl]-piperidin-1-yl}-methanone,
- (3-Chloro-4-fluoro-phenyl)-{4-fluoro-4-[(3,4-dihydro-2H-8-methoxy-1,4-benzoxazine-2-methanamino)-methyl]-piperidin-1-yl}-methanone,
- (3-Chloro-4-fluoro-phenyl)-{4-fluoro-4-[(3,4-dihydro-2H-8-cyano-1,4-benzoxazine-2-methanamino)-methyl]-piperidin-1-yl}-methanone,
- (3-Chloro-4-fluoro-phenyl)-{4-fluoro-4-[(3,4-dihydro-2H-4-methyl-1,4-benzoxazine-2-methanamino)-methyl]-piperidin-1-yl}-methanone,
- (3-Chloro-4-fluoro-phenyl)-{4-fluoro-4-[(3,4-dihydro-2H-8-carbamoyl-1,4-benzoxazine-2-methanamino)-methyl]-piperidin-1}-methanone.

7. A method of treating pain, which comprises administering to a patient in need thereof an effective amount of a compound according to claim 1.

8. The method according to claim 7, wherein said pain is pathological pain and/or physiological pain.

9. A method of treating depression, which comprises administering to a patient in need thereof an effective amount of a compound according to claim 1.

10. Pharmaceutical composition comprising at least one compound of formula (1) according to claim 1 in combination with one or more suitable and pharmaceutically acceptable excipients, adjuvants or vehicles.

11. Method to prepare compounds of formula (1)

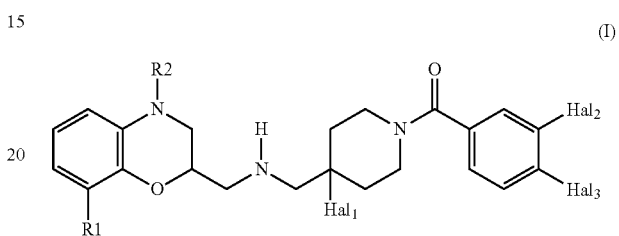

(I)

wherein the radicals $R_1$, $R_2$, $Hal_1$, $Hal_2$ and $Hal_3$ have the designations given in claim 1, which comprises
condensing an intermediate of type 3,4-dihydro-2H-1,4-benzoxazine-2-methanamine of formula (2)

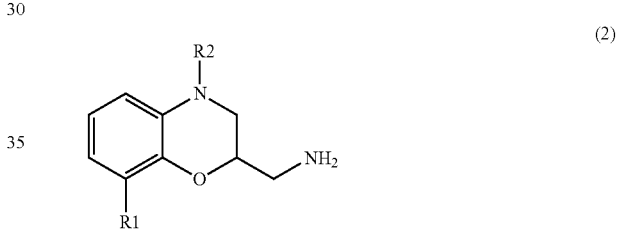

(2)

in which R1 and $R_2$ have the designations given previously for formula (1), and cyanohydrine of formula (3)

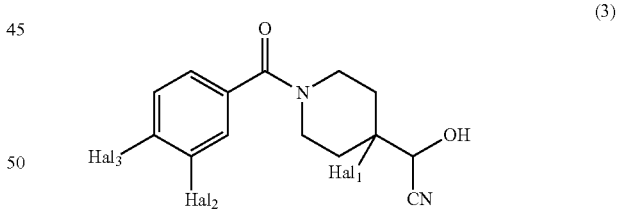

(3)

in which $Hal_1$, $Hal_2$ and $Hal_3$ have the designations given previously for formula (1), in the presence of a reducing agent and optionally a base.

* * * * *